United States Patent [19]
Dow et al.

[11] Patent Number: 4,738,842
[45] Date of Patent: Apr. 19, 1988

[54] TOPICAL ANTIINFLAMMATORY COMPOSITIONS

[75] Inventors: Gordon J. Dow, San Rafael, Calif.; Helen J. Schultz, Falcon Heights, Minn.

[73] Assignee: Riker Laboratories, St. Paul, Minn.

[21] Appl. No.: 819,757

[22] Filed: Jan. 17, 1986

[51] Int. Cl.$^4$ .................. A61U 31/78; A61U 31/44
[52] U.S. Cl. ...................................... 424/81; 514/282
[58] Field of Search ......................... 424/81; 514/282

[56] References Cited
U.S. PATENT DOCUMENTS
4,172,082 10/1979 Moore ................................. 549/72

FOREIGN PATENT DOCUMENTS
0130516 6/1984 European Pat. Off. .

Primary Examiner—Stanley J. Friedman
Attorney, Agent, or Firm—Donald M. Sell; James A. Smith; Robert W. Sprague

[57] ABSTRACT

Novel topical creams or lotions containing 2,6-di-t-butyl-4-(2'-thenoyl)phenol exhibiting good skin penetrability are disclosed.

4 Claims, 1 Drawing Sheet

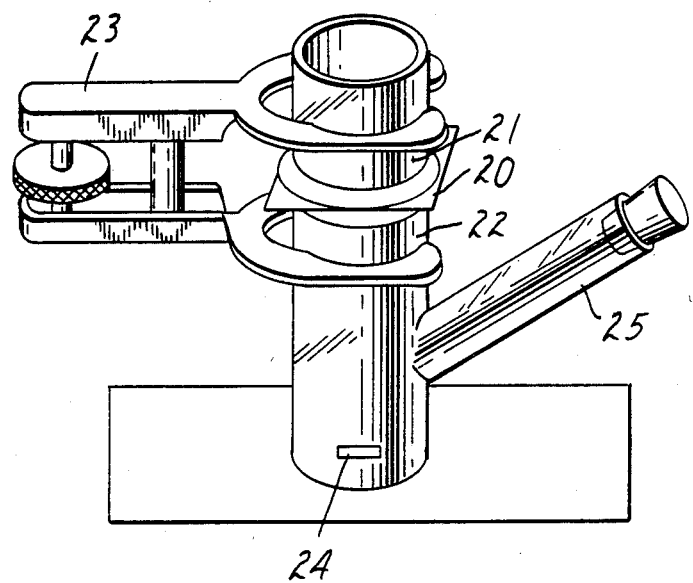

TOPICAL ANTIINFLAMMATORY COMPOSITIONS

TECHNICAL FIELD

This invention relates to novel topical antiinflammatory compositions. More specifically, this invention relates to topical compositions containing 2,6-di-t-butyl-4-(2'-thenoyl)phenol as the antiinflammatory agent.

BACKGROUND OF THE INVENTION

The compound 2,6-di-t-butyl-4-(2'-thenoyl)phenol is disclosed in U.S. Pat. No. 4,172,082 as an antiinflammatory agent. The said U.S. patent discloses that the compound may be administered topically in the form of creams or gels. Comparative Example 4 herein describes a cream formulation which was tested clinically and contained 2,6-di-t-butyl-4-(2'-thenoyl)phenol.

Extensive research has now resulted in a substantially improved formulation (Example 1) of this invention which is chemically and physically stable, non-irritating and provides good skin penetrability of the 2,6-di-t-butyl-4-(2'-thenoyl)phenol. Notably, said formulation exhibits a superior degree of in vitro skin penetrability as compared to the prior art cream of Comparative Example 4.

BRIEF DESCRIPTION OF THE INVENTION

The present invention provides novel, substantially non-irritating antiinflammatory cream or lotion formulations comprising an oil phase and a water phase in admixture, the oil phase comprising:

(a) the antiinflammatory compound 2,6-di-t-butyl-4-(2'-thenoyl)phenol in an amount of about 0.25% to 3% by weight based on the total weight of the cream or lotion; and (b) an emollient and solvent component comprising diisopropyl adipate, benzyl alcohol and cetyl alcohol; the oil phase being further characterized in that it comprises a substantially saturated solution of the antiinflammatory compound, and is present in an amount of about 0.5 to 60% by weight based on the total weight of the cream or lotion; and the water phase comprising:

(a) one or more surface active emulsifiers which are present in a total amount of about 0.05 to 10% by weight based on the total weight of the cream or lotion; and (b) water in an amount of about 10% to 99.5% by weight based on the total weight of the cream or lotion; the cream or lotion being further characterized in that, when tested in the hairless mouse skin test (the Test Method referred to hereinafter), it provides skin penetration of the antiinflammatory compound of at least about 5% of the dose applied.

The creams and lotions of this invention provide a superior degree of skin penetrability.

BRIEF DESCRIPTION OF THE DRAWING

The invention may be better understood by reference to the accompanying drawing wherein:

The drawing is an isometric view of a diffusion cell for measuring penetrability of 2,6-di-t-butyl-4-(2'-thenoyl)phenol across skin.

DETAILED DESCRIPTION OF THE INVENTION

The present invention relates to topical antiinflammatory creams or lotions containing 2,6-di-t-butyl-4-(2'-thenoyl)phenol which provide substantially improved in vitro skin penetrability of the 2,6-di-t-butyl-4-(2'-thenoyl)phenol.

By the use of the phrase "substantially non-irritating" herein is meant that the creams and lotions of the invention do not cause unacceptable skin irritation in conventional repeat skin irritation tests in albino rabbits such as that described in Draize et al., "Appraisal of the Safety of Chemicals in Food, Drugs and Cosmetics", prepared by the Division of Pharmacology of the Food and Drug Administration, and published originally in 1959 by the Association of Food and Drug Officials of the United States, Topeka, Kans. (2nd printing 1965), incorporated herein by reference.

The creams and lotions of the invention comprise an oil phase and a water phase as follows:

The oil phase comprises the antiinflammatory compound 2,6-di-t-butyl-4-(2'-thenoyl)phenol and an emollient and solvent component comprising diisopropyl adipate, benzyl alcohol and cetyl alcohol. The compound 2,6-di-t-butyl-4-(2'-thenoyl)phenol is a known antiinflammatory agent which may be prepared using the method disclosed in U.S. Pat. No. 4,172,082, incorporated herein by reference. Diisopropyl adipate and benzyl alcohol function as solvents for the antiinflammatory compound while cetyl alcohol is an emollient.

The amount of 2,6-di-t-butyl-4-(2'-thenoyl)phenol present in the creams and lotions of the invention is about 0.25 to 3% by weight based on the total weight of the cream or lotion. Preferably, the antiinflammatory compound will be present in an amount of about 0.5 to 1.5% by weight based on the total weight of the cream or lotion.

The amounts of diisopropyl adipate, benzyl alcohol and cetyl alcohol of the emollient and solvent component will generally be as follows. Diisopropyl adipate will generally be present in an amount by weight of about 0.1 to 45% based on the total weight of the cream or lotion. Benzyl alcohol will generally be present in an amount by weight of about 0.1 to 40% based on the total weight of the cream or lotion. Cetyl alcohol will generally be present in an amount by weight of about 0.1 to 10% based on the total weight of the cream or lotion.

In order to achieve a high degree of skin penetration of 2,6-di-t-butyl-4-(2'-thenoyl)phenol, the various components of the oil phase are used in amounts which provide a substantially saturated solution of the antiinflammatory compound in the oil phase. By a "substantially saturated solution" is meant that the antiinflammatory compound is present in the oil phase in an amount to provide at least about 50% of the maximum amount of the antiinflammatory compound which would be soluble in the oil phase at room temperature. Further, the oil phase is present in an amount by weight of about 0.5 to 60% based on the total weight of the cream or lotion.

As for the water phase of the creams and lotions of the invention, it comprises one or more surface active emulsifiers and water. The surface active emulsifier(s) may be anionic or nonionic, but will preferably be of the former type. Generally, the surface active emulsifier(s) will be present in a total amount by weight of about 0.05 to 10% by weight based on the total weight of the cream or lotion. The preferred surface active emulsifier is Carsonol ® SLES-2, a sodium lauryl ether 2 sulfate available from Lonza, Inc., Fairlawn, N.J.

Water is generally present in the creams and lotions of the invention in an amount by weight of about 10 to 99.5% based on the total weight of the cream or lotion.

While benzyl alcohol is an antimicrobial agent, the creams and lotions may further comprise other preservatives such as methylparaben and propylparaben. The appropriate amount of such preservative(s) will be known to one skilled in the art.

Humectants such as glycerin may also be advantageously employed in the creams and lotions of the invention. Again, appropriate amounts will be known to those skilled in the art.

Creams and lotions may be conveniently prepared by including a thickener such as a water-soluble, acrylic acid polymer having a molecular weight in the range of approximately 1,000,000 to 4,000,000. Examples of such polymers are Carbopol ® polymers 934, 934P, 940 and 941, all of which are available from B. F. Goodrich Company. Such polymers may be included in the cream in an amount of about 0.2 to 3.5% by weight based on the weight of the total cream. Cross-linking of the polymer to provide thickening is achieved by neutralizing it during preparation of the cream with a suitable base such as potassium hydroxide.

A suitable base such as potassium hydroxide or a suitable acid such as citric acid may also be employed to adjust the pH of the cream or lotion to the desired level.

The oil phase of the creams and lotions of the invention is generally prepared by first heating the emollient and solvent component and then adding the antiinflammatory compound thereto. Complete dissolution of the antiinflammatory compound should be achieved before the oil and water phases are combined.

To prepare the water phase, the ingredients such as surfactant, preservative and humectant are added to water. However, if a Carbopol ® polymer or the like is to be present, generally that polymer is first dispersed in the water and hydrated using vigorous agitation prior to the addition of the other ingredients. Cross-linking of the polymer can be accomplished by adjusting the pH before or after the water and oil phases are combined.

The creams and lotions of the invention are generally prepared by combining the phases at an elevated temperature, for example, 50° to 55° C. The resulting emulsion is mixed with a suitable mixer apparatus to give the desired cream or lotion.

The pH of the formulation should be in the range of about 3.5 to 8.5, and will preferably be in the range of 4.5 6.5. If the pH is not already at the desired level after the phases have been combined, it should be adjusted.

Although animal skins are known to give significant quantitative differences in drug penetrability versus human skin, a rank order correlation is generally observed with various drugs (M. J. Bartek and J. A. LaBudde in "Animal Modes in Dermatology", H. Maibach, Ed., Churchill Livingstone, New York, 1975, pp. 103–119). Hairless mouse skin has been recommended as a readily available animal skin for use in diffusion cells with steroids and small molecules (R. B. Stoughton, Arch. Derm., 99, 753 (1969), J. L. Cohen and R. B. Stoughton, J. Invest. Derm. 62, 507 (1974), R. B. Stoughton in "Animal Modes in Dermatology", H. Maibach, Ed., Churchill Livingstone, New York, 1975, pp. 121–131).

In the specific test procedure used herein (referred to herein as "Test Method"), hairless mouse skin removed from female hairless mice (available from Jackson Laboratory, Strain HRS/J), age 40–80 days, is used. The skin is maintained on ice until use which should be within 8 hours of sacrifice. The mouse skin is cut in half and each half is mounted, or the skin is used whole, on a diffusion cell of the type shown in the drawing. The cell is modeled after those described in the literature, e.g., J. L. Cohen, R. B. Stoughton, J. Invest. Dermatol., 62, 507 (1974) and R. B. Stoughton, Arch. Derm., 99, 753 (1964), and has an inner diameter of 1.5 centimeters. As shown in the figure, the mouse skin 20 is mounted epidermal side up between the upper and lower portions of the cell 21 and 22, which are held together by a means of a ball joint clamp 23. The cell below the skin is filled completely with a 75% solution of polyethylene glycol (400 Carbowax ® 400) available from Union Carbide) in water so that the acceptor fluid contacts the skin. The acceptor fluid is stirred using a magnetic stirring bar 24 and a magnetic stirrer (not illustrated). The sampling port 25 is stoppered or covered with a material such as Parafilm ® except when in use.

Approximately 100 mg of a formulation to be evaluated is applied to the epidermal (upper) side of the skin to cover only the area of skin (i.e., approximately 1.77 centimeters$^2$) which will be in contact with the acceptor fluid in an even layer while the skin is mounted in the diffusion cell. Generally, the formulation is applied to the skin prior to the time the acceptor fluid is added to the cell below the skin.

The cell is then placed in a constant temperature (35±2° C.), constant humidity chamber maintained at 50±10 percent relative humidity and kept within that range throughout the experiment (i.e., 24 hours). The chamber utilizes a heat exchanger coupled to a constant temperature bath, with a fan to circulate air. A saturated calcium nitrate solution is used to maintain the humidity. The acceptor fluid is stirred by means of a magnetic stirring bar throughout the experiment to assure a uniform sample and a reduced diffusion layer on the dermal side of the skin. The acceptor fluid is removed at 24 hours. The withdrawn acceptor fluid is analyzed for drug content by conventional high pressure liquid chromatography as follows: A 15 centimeter column containing Zorbax ® $C_8$ (an octylsilane, available from E. I. DuPont de Nemours & Company), 5 micron particle size, is used. The mobile phase constitutes 80% methanol:20% water and the flow rate is 2 ml per minute. Ultraviolet detection at 313 nanometers is used. The amount of the drug penetrating the skin over the 24-hour period is calculated as a percentage of the dose applied.

In this Test Method, the formulation to be tested is tested on 4 skins on each of four consecutive days, and the results are averaged.

The following examples are provided to illustrate the invention, and are not intended to limit the invention. All amounts are expressed as percent by weight unless otherwise indicated.

Example 1

A cream according to the present invention was prepared from the following ingredients:

| Oil Phase | % by Weight | Amount |
|---|---|---|
| Diisopropyl adipate | 5.0 | 20.0 g |
| Benzyl alcohol | 2.0 | 8.0 g |
| Cetyl alcohol | 2.0 | 8.0 g |
| 2,6-di-t-butyl-4-(2'-thenoyl)phenol | 1.0 | 4.0 g |

| Oil Phase | % by Weight | Amount |
|---|---|---|
| Aqueous Phase | | |
| Carsonal ® SLES-2 (sodium lauryl ether 2 sulfonate available from Lonza, Inc., Fairlawn, NJ) | 0.5 | 2.0 g |
| Carbopol ® 934 (Carbomer 934, an acrylic acid polymer available from B. F. Goodrich) | 1.5 | 6.0 g |
| Parabens in glycerin* | 3.0 | 12.0 g |
| Purified water | 81.75 | 327.0 g |
| Potassium hydroxide (10% in water) | 3.25 | 13.0 g |

*prepared by combining 5% methylparaben, 2.5% propylparaben and 92.5% glycerin, heating to 40° C. and stirring until dissolved.

The materials listed above were combined in accordance with the following procedures:

In a tared beaker, the Carbopol ® was gradually added to the purified water using a high speed mixer. The mixing was continued for a minimum of 30 minutes to insure hydration of the Carbopol ®. The parabens in glycerin and the Carsonol ® SLES-2 were added and the resulting mixture was heated to 65° C. In a separate beaker, the diisopropyl adipate and benzyl alcohol and cetyl alcohol were combined and heated to 65° C. The 2,6-di-t-butyl-4-(2'-thenoyl)phenol was dissolved in the hot oil phase. Just prior to combining phases, water was added to the water phase to account for that lost to evaporation. With both phases at approximately the same temperature (50°-55° C.), the oil phase was added to the aqueous phase using a high speed mixer. The mixing was continued at high speed for 3 to 4 minutes. The speed of the mixer was reduced and the potassium hydroxide was carefully added. The mixture was allowed to cool while mixing. The pH was checked and adjusted as necessary to a pH of 5.5±0.5. Additional water was added to make a final weight of 400.0 g. The mixture was mixed with a suitable mixer until uniform to give a white cream.

This medium viscosity cream was stable and non-irritating. It was cosmetically elegant with excellent skin feel; it lubricated the skin well, but did not feel greasy. When tested in accordance with the Test Method referred to previously, the cream provided an average of 8.34±2.97 percent skin penetration of the antiinflammatory compound.

COMPARATIVE EXAMPLES 2-5

The following comparative formulations were prepared:

COMPARATIVE EXAMPLE 2

A solution was prepared by dissolving 1.0 g of 2,6-di-t-butyl-4-(2'-thenoyl)phenol in a sufficient quantity of a mixture of 5% propylene glycol by weight and 95% isopropyl alcohol by weight to make 100 ml of solution.

COMPARATIVE EXAMPLE 3

An ointment was prepared containing 1.0% 2,6-di-t-butyl-4-(2'-thenoyl)phenol by weight, 2.0% light mineral oil by weight and 97.0% white petrolatum by weight. The antiinflammatory compound was ground using a mortar and pestle. The material was levigated with the light mineral oil. The petrolatum was then geometrically added to the above in the mortar with mixing.

COMPARATIVE EXAMPLE 4

A cream was prepared containing 1.0% 2,6-di-t-butyl-4-(2'-thenoyl)phenol by weight, 26.4% polyoxyethylene 4 lauryl ether (Brij ® 30SP, available from ICI Americas, Inc.), 13.4% caprylic/capric triglyceride (Neobee ® 0, available from PVO International, Inc., N.Y., N.Y.), 14.5% aluminum starch octenyl succinate (Dry Flo ®, available from National Starch Chemical Corp.), 0.2% sorbic acid, 0.2% methylparaben, 0.1% propylparaben and 44.2% purified water.

The Brij ® 30SP, Neobee ® 0, parabens, sorbic acid and antiinflammatory compound were combined and heated until all material was in solution. The Dry Flo ® starch was then added and the resulting mixture was stirred until uniform. The water was thereafter added with stirring and mixed until uniform.

COMPARATIVE EXAMPLE 5

A cream was prepared containing 1.0% by weight 2,6-di-t-butyl-4-(2'-thenoyl)phenol, 15.4% by weight propylene glycol dipelargonate, 8.0% stearic acid, 1.0% triethanolamine, 2.0% cetyl alcohol, 1.0% Carbopol ® 934, 0.15% methylparaben, 0.075% propylparaben, 2.775% glycerin, 0.15% sodium lauryl ether 2 sulfate and 68.45% purified water.

In a tared beaker, the Carbopol ® 934 was gradually added to the water using a high speed mixer. Mixing continued for 30 minutes and any water lost to evaporation was then replaced. A mixture of the parabens and glycerin was prepared as in Example 1. The parabens in glycerin and the Carsonol ® SLES-2 were added to the above, and the mixture was heated to 65° C. In a second beaker, the propylene glycol dipelargonate, stearic acid and cetyl alcohol were heated to 65° C. The antiinflammatory compound was then added to the above oil phase with mixing to achieve dissolution. Using a high speed mixer, the oil phase was added to the water phase, and mixing was continued for 3 to 4 minutes. The triethanolamine was then added, and the mixture was mixed well. The mixture was hand-stirred while it was allowed to cool.

The above formulations of Comparative Examples 2-5 were tested in accordance with the Test Method referred to previously, except that in the case of these Comparative Examples, the humidity ranged from about 40 to 73% and the number of skins involved differed. The results of the tests were as follows:

| Formulation | Number of Skins | % Penetration in 24 hours |
|---|---|---|
| Comparative Example 2 | 2[a] | 0.80 ± 0.40 |
| Comparative Example 3 | 4[b] | 0.46 ± 0.25 |
| Comparative Example 4 | 8[c] | 1.41 ± 0.45 |
| Comparative Example 5 | 18[d] | 2.45 ± 1.21 |

[a]The two skins were run on the same day
[b]The four skins were run on the same day
[c]The eight skins were run on the same day
[d]The eighteen skins were run on four non-consecutive days in groups of 4, 4, 4, 4, and 2

As can be seen from the above results, the cream of Example 1 of the invention exhibited a superior degree of skin penetrability as compared to all of the above comparative formulations.

What is claimed:

1. A substantially non-irritating, antiinflammatory cream or lotion comprising an oil phase and a water phase in admixture, said oil phase comprising:

(a) the antiinflammatory compound 2,6-di-t-butyl-4-(2'-thenoyl)phenol in an amount of about 0.25% to 3% by weight based on the total weight of said cream or lotion; and (b) an emollient and solvent component comprising diisopropyl adipate in an amount of about 0.1 to 45% by weight based on the total weight of the cream or lotion, benzyl alcohol in an amount of about 0.1 to 40% by weight based on the total weight of the cream or lotion and cetyl alcohol in an amount of about 0.1 to 10% by weight based on the total weight of the cream or lotion;

said oil phase being further characterized in that it comprises a substantially saturated solution of said antiinflammatory compound and is present in an amount of about 0.5 to 60% by weight based on the total weight of said cream or lotion; and said water phase comprising:

(a) one or more surface active emulsifiers which are anionic or nonionic and which are present in a total amount of about 0.05 to 10% by weight based on the total weight of said cream or lotion; and (b) water in an amount of about 10 to 99.5% by weight based on the total weight of said cream or lotion;

said cream or lotion being further characterized in that, when tested in accordance with the Test Method, it provides skin penetration of said antiinflammatory compound of at least about 5% of the applied dose.

2. A cream or lotion according to claim 1, wherein said antiinflammatory compound is present in an amount of about 0.5 to 1.5% by weight based on the total weight of said cream or lotion.

3. A cream or lotion according to claim 1, wherein said cream or lotion further comprises, as a thickener, an acrylic acid polymer having a molecular weight of about 1,000,000 to 4,000,000, said acrylic acid polymer being present in an amount of about 0.2 to 3.5% by weight based on the total weight of said cream or lotion, where said cream or lotion further exhibits a pH of about 3.5 to 8.5.

4. A cream according to claim 1, comprising, by weight, about 1% of said antiinflammatory compound, about 5% of diisopropyl adipate, about 2% of benzyl alcohol, about 2% cetyl alcohol, about 0.15% sodium lauryl ether 2 sulfate, about 1.5% carbomer 934P, about 0.15% methylparaben, about 0.075% propylparaben, about 2.775% glycerin, about 0.325% potassium hydroxide and about 85.025% purified water.

* * * * *